(12) United States Patent
Lamprecht et al.

(10) Patent No.: US 12,226,574 B2
(45) Date of Patent: Feb. 18, 2025

(54) USER INTERFACE AND METHOD FOR OPERATING A BREATHING APPARATUS

(71) Applicant: Fisher & Paykel Healthcare Limited, Auckland (NZ)

(72) Inventors: Bernhard Florian Lamprecht, Auckland (NZ); Andrew Paul Maxwell Salmon, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/309,588

(22) Filed: Apr. 28, 2023

(65) Prior Publication Data

US 2024/0091469 A1  Mar. 21, 2024

Related U.S. Application Data

(63) Continuation of application No. 14/913,076, filed as application No. PCT/IB2014/063961 on Aug. 19, 2014, now Pat. No. 11,672,931.

(Continued)

(51) Int. Cl.
*A61M 16/00* (2006.01)
*A61M 16/16* (2006.01)
(Continued)

(52) U.S. Cl.
CPC .... *A61M 16/0066* (2013.01); *A61M 16/0051* (2013.01); *A61M 16/0069* (2014.02);
(Continued)

(58) Field of Classification Search
CPC .......... A61M 16/0066; A61M 16/0069; A61M 16/021; A61M 16/0051; A61M 16/16;
(Continued)

(56) References Cited

U.S. PATENT DOCUMENTS 5,168,316 A * 12/1992 Hino ................. G03G 15/6508
271/9.03
5,677,708 A  10/1997 Matthews, III et al.
(Continued)

FOREIGN PATENT DOCUMENTS

AU  2014310320  3/2016
EP  3033129  6/2016
(Continued)

OTHER PUBLICATIONS

Casio: "Operation Guide 3353 3354 5053 1 MO0804-EA", Feb. 2, 2013 (Feb. 2, 2013), XP055351540, Retrieved from the Internet: URL: http://support.casio.com/en/manual/009qw5053.pdf [retrieved on Mar. 3, 2017].

*Primary Examiner* — Daniel Samwel
(74) *Attorney, Agent, or Firm* — VIA LLP

(57) ABSTRACT

A breathing apparatus with a user interface comprising a display for displaying at least one menu item, a first button operable to sequentially cycle through and display a plurality of menu items, a second and optionally third button operable to configure a parameter of the selected menu item, and a fourth button operable to confirm the change of a parameter of the selected menu item, wherein the parameter is a respiratory parameter and/or other breathing apparatus parameter.

18 Claims, 6 Drawing Sheets

Related U.S. Application Data

(60) Provisional application No. 61/867,257, filed on Aug. 19, 2013.

(51) Int. Cl.

| | | |
|---|---|---|
| *G06F 3/02* | (2006.01) | |
| *G06F 3/0482* | (2013.01) | |
| *G06F 3/04847* | (2022.01) | |
| *A61M 16/10* | (2006.01) | |

(52) U.S. Cl.
CPC .......... *A61M 16/021* (2017.08); *A61M 16/16* (2013.01); *G06F 3/02* (2013.01); *G06F 3/04847* (2013.01); *A61M 16/1095* (2014.02); *A61M 2205/15* (2013.01); *A61M 2205/18* (2013.01); *A61M 2205/502* (2013.01); *A61M 2205/52* (2013.01); *G06F 3/0482* (2013.01)

(58) Field of Classification Search
CPC .......... A61M 16/1095; A61M 2205/15; A61M 2205/18; A61M 2205/502; A61M 2205/52; G06F 3/02; G06F 3/04847; G06F 3/0482

See application file for complete search history.

(56) References Cited

U.S. PATENT DOCUMENTS

| | | | |
|---|---|---|---|
| 6,201,540 B1 | 3/2001 | Gallup et al. | |
| 6,490,678 B1 * | 12/2002 | Aquilar | G06F 9/4406 |
| | | | 715/969 |
| 8,655,345 B2 | 2/2014 | Gold | |
| 8,944,057 B2 | 2/2015 | Hill et al. | |
| 11,672,931 B2 | 6/2023 | Lamprecht et al. | |
| 2002/0163543 A1 | 11/2002 | Oshikiri | |
| 2003/0011640 A1 | 1/2003 | Green et al. | |
| 2003/0177205 A1 | 9/2003 | Liang et al. | |
| 2004/0190129 A1 | 9/2004 | Peter et al. | |
| 2006/0248477 A1 | 11/2006 | Boukhny et al. | |
| 2007/0008239 A1 * | 1/2007 | Stroupe | H04M 1/0214 |
| | | | 345/1.1 |
| 2007/0060392 A1 | 3/2007 | Sullivan | |
| 2007/0266334 A1 | 11/2007 | Donaldson | |
| 2007/0270921 A1 | 11/2007 | Strother et al. | |
| 2008/0072896 A1 * | 3/2008 | Setzer | G16Z 99/00 |
| | | | 128/200.24 |
| 2008/0072902 A1 | 3/2008 | Setzer et al. | |
| 2008/0128523 A1 | 6/2008 | Hoglund et al. | |
| 2008/0290183 A1 * | 11/2008 | Laberge | G05D 23/1931 |
| | | | 236/94 |
| 2009/0005651 A1 * | 1/2009 | Ward | A61B 5/00 |
| | | | 600/300 |
| 2009/0054743 A1 | 2/2009 | Stewart | |
| 2009/0090363 A1 | 4/2009 | Niland et al. | |
| 2009/0140056 A1 | 6/2009 | Leen | |
| 2010/0011307 A1 * | 1/2010 | Desfossez | G06F 3/0489 |
| | | | 715/764 |
| 2010/0078026 A1 | 4/2010 | Andrieux et al. | |
| 2010/0199102 A1 | 8/2010 | Knepper et al. | |
| 2010/0211219 A1 | 8/2010 | Hallin | |
| 2010/0229867 A1 | 9/2010 | Bertinetti et al. | |
| 2011/0164002 A1 | 7/2011 | Hill et al. | |
| 2012/0017904 A1 * | 1/2012 | Ratto | A61M 16/024 |
| | | | 128/207.18 |
| 2012/0138058 A1 | 6/2012 | Fu et al. | |
| 2012/0179006 A1 | 7/2012 | Jansen et al. | |
| 2012/0293014 A1 | 11/2012 | Wang | |
| 2013/0104120 A1 * | 4/2013 | Arrizza | G16H 20/17 |
| | | | 717/173 |
| 2013/0104892 A1 * | 5/2013 | Steinhauer | G16H 20/40 |
| | | | 128/204.18 |
| 2013/0263046 A1 | 10/2013 | Takahashi | |
| 2015/0020801 A1 | 1/2015 | Frame et al. | |
| 2015/0157818 A1 | 6/2015 | Darby et al. | |
| 2015/0160845 A1 | 6/2015 | Lahtivuori et al. | |
| 2017/0076634 A1 | 3/2017 | Hoss et al. | |

FOREIGN PATENT DOCUMENTS

| | | | |
|---|---|---|---|
| GB | 2533503 | 6/2016 | |
| WO | WO-2006126900 A1 * | 11/2006 | ........ A61M 16/0003 |
| WO | WO 2015/025264 | 2/2015 | |

\* cited by examiner

USER INTERFACE AND METHOD FOR OPERATING A BREATHING APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF INVENTION

The present invention relates to a user interface and method of operating a user interface of a breathing apparatus.

BACKGROUND

Breathing apparatus can be used to assist breathing of patients. Examples of breathing apparatus include CPAP machines, which are used for patients with OSA, and flow therapy machines, which are used for patients with COPD or other lung/breathing disorders.

Breathing apparatus are often used by elderly, frail and/or sick people and/or people who are not technologically capable. User interfaces of breathing apparatus can be difficult to use for such people.

SUMMARY OF INVENTION

It is an object of the present invention to provide patients with a breathing apparatus that might be easier to use, or at least provide the public with a useful choice.

In one aspect the present invention may be said to consist in a breathing apparatus with a user interface comprising a display for displaying at least one menu item, a first button operable to sequentially cycle through and display a plurality of menu items, a second and optionally third button operable to configure a parameter of the selected menu item, and a fourth button operable to confirm the change of a parameter of the selected menu item, wherein the parameter is a respiratory parameter and/or other breathing apparatus parameter.

Preferably the fourth button is operable to cause the display to display a home screen/first menu item from the selected menu item.

Preferably the second button is operable to increase the value of the parameter and the third button is operable to decrease the value of the parameter.

Preferably the fourth button is operable to confirm the parameter configuration.

Preferably the fourth button to confirm the parameter configuration, the display displays a home screen/first menu item.

Preferably after operating the second and/or third button the first button is operable to reject the parameter configuration.

Preferably after operating the first button to reject the parameter configuration, the display displays a home screen/first menu item.

Preferably the second button and/or third button is/are operable to sequentially cycle through and display a plurality of lower level menu items.

Preferably after operating the second and/or third button, the first or the fourth button are operable to display the home screen/first menu item on the display.

Preferably the user interface further comprises a power button for activating the blower and/or exiting a standby mode to commence respiratory therapy, or alternatively deactivating the blower and/or entering a standby mode.

Preferably the power button is triggered by holding the button instantly or for a period longer than a predetermined amount of time, such as one minute.

Preferably the power button is triggered by operating the button several times in rapid succession.

Preferably the display comprises one or more screens, which optionally might be colour.

Preferably the menu item and/or parameter relate to one or more of: information relating to user and device data; humidity such as level of humidification; treatment pressure; ramp time; automatic ramp; wakefulness dependent pressure control; temperature control; heated tube temperature; clock and time settings; an alarm with setting options for the alarm; screen brightness; leak such as mask leak and threshold for responding to mask leak; notification relating to presence of peripherals such as USB or network connection; images relating to user feedback and vendor logos.

Preferably the display is for displaying a single menu item at one time.

Alternatively the display is for displaying two or more menu items at one time.

Preferably one of the second and third buttons could be marked with one of:
An upwards arrow or triangle;
"UP".

Preferably one of the second and third buttons could be marked with one of:
An downwards arrow or triangle;
"DOWN".

Preferably the breathing apparatus is a CPAP apparatus and the respiratory parameter is CPAP parameter.

In another aspect the present invention may be said to consist in a method of operating a breathing apparatus comprising a display for displaying one or more menu item(s), and at least four buttons, the method comprising the steps of:
 (a) displaying one of a set of menu items,
 (b) receiving input from a first button being pressed,
 (c) displaying the next in the set of menu items,
 (d) receiving input from either a second or third button being pressed, and
 (e) displaying a change in parameter associated with the displayed menu item, and/or
 (f) displaying data or a menu time from a lower level menu,
wherein the parameter is a respiratory parameter and/or other breathing apparatus parameter.

Preferably the method further comprises the steps of:
 (g) receiving input from a fourth button,
 (h) optionally confirming the change in parameter,
 (i) displaying the home screen/first menu item.

Preferably the method further comprises the steps of:
receiving input from the first button,
displaying a home screen/first menu item of the set of menu items and/or rejecting the change in parameter.

Preferably after sequentially cycling through and displaying the plurality of menu items, the first menu item is displayed again.

Preferably after sequentially cycling through and displaying the set of menu items, the first menu item is displayed again.

The term "comprising" as used in this specification means "consisting at least in part of". When interpreting statements in this specification which include that term, the features prefaced by that term in each statement all need to be present, but other features can also be present. Related terms such as "comprise" or "comprised" are to be interpreted in the same manner.

The term "and/or" means "and", "or" or "both".

As used herein, the order in which the steps of the method that is described herein are listed do not indicate the only order in which the steps are carried out. The steps can be carried out in any order, and may be carried out simultaneously.

The invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF DRAWINGS

Preferred embodiments of the present invention will now be described, by way of example only, with reference to the accompanying drawings, in which.

DETAILED DESCRIPTION OF EMBODIMENTS

First Embodiment

Figure 1:
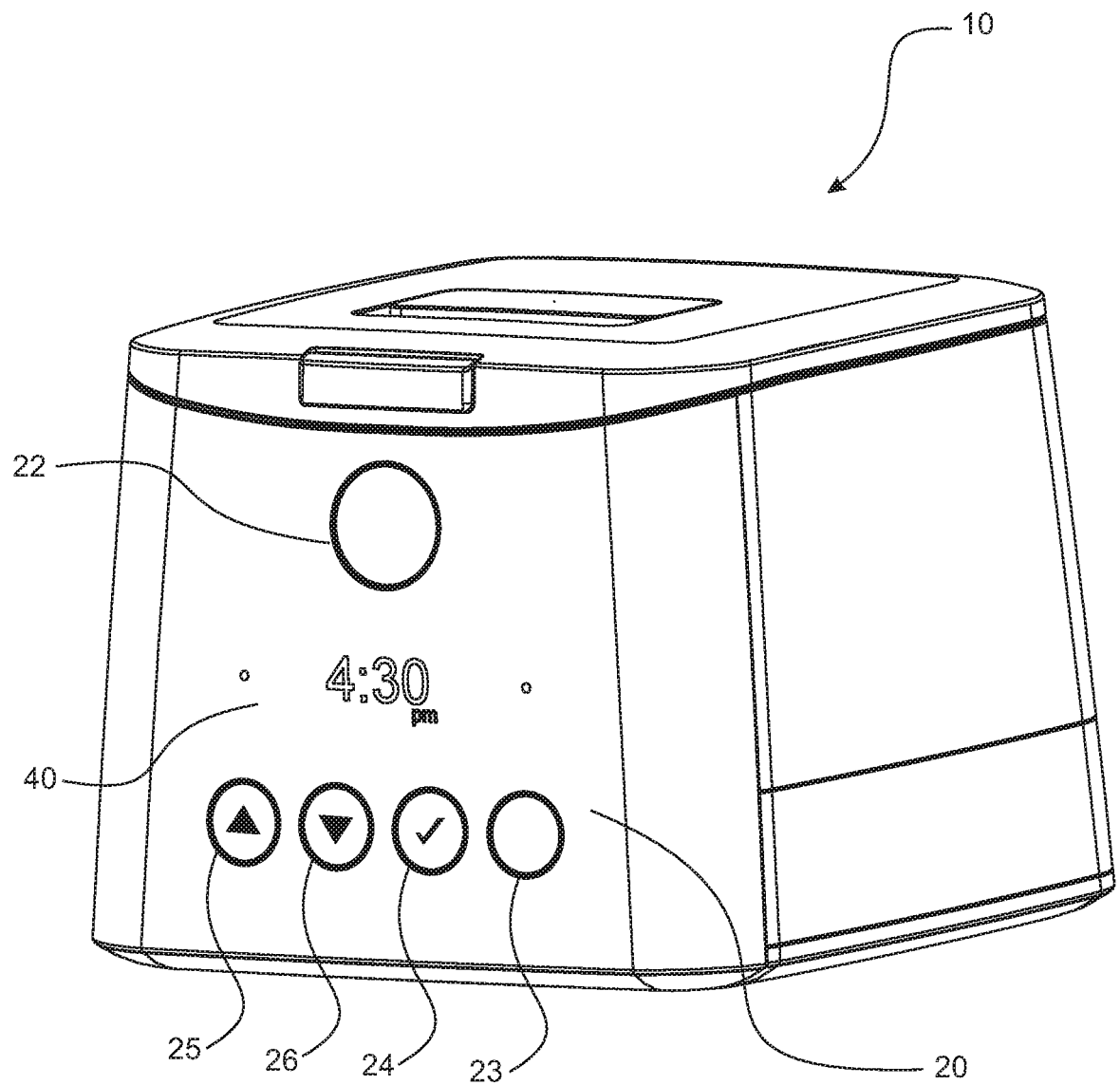
FIG. 1 is a perspective view of a breathing apparatus having a user interface of the preferred embodiment.
Figure 2:
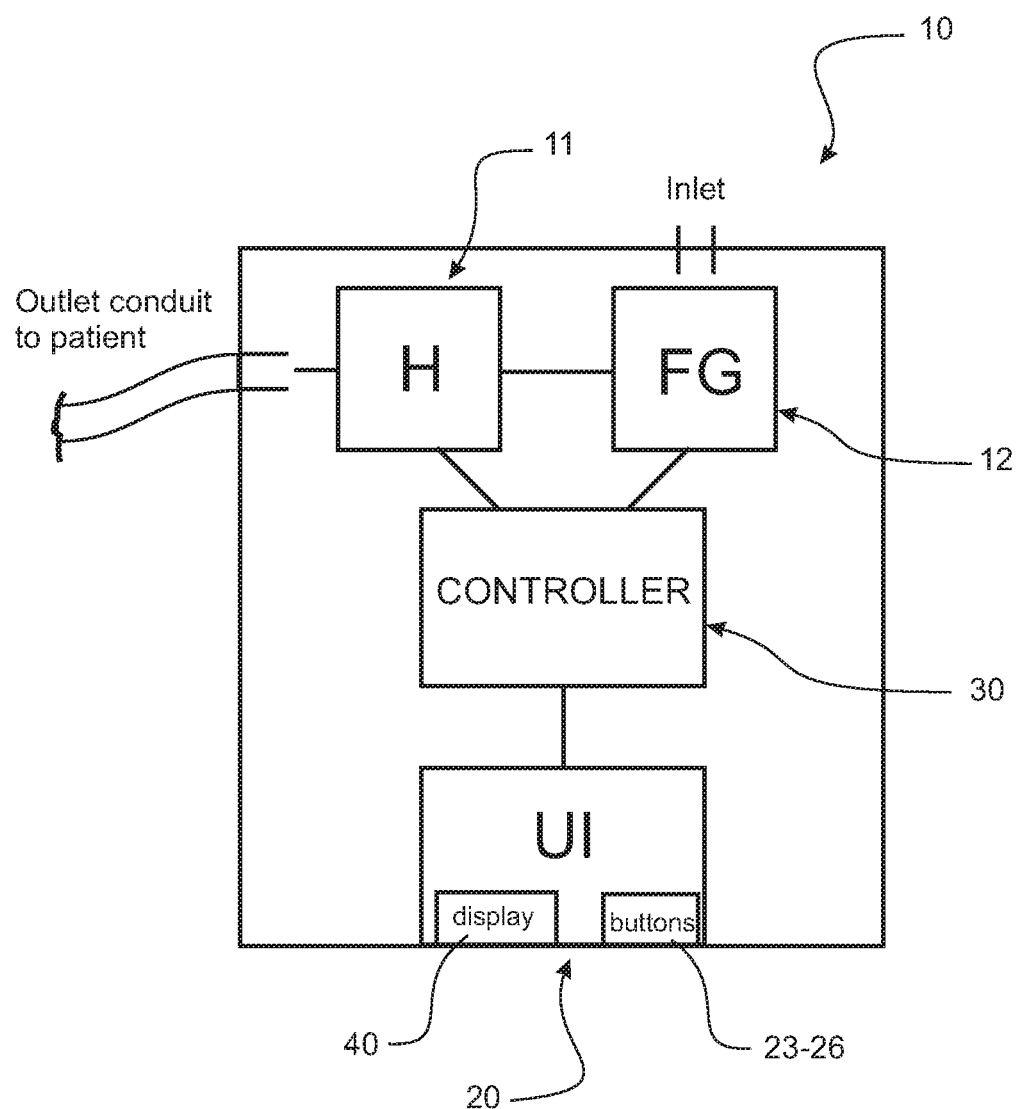
FIG. 2 is a schematic view of the components for the breathing apparatus of FIG. 1.

FIG. 1 shows the external form of a breathing apparatus 10 (in this case a continuous positive airway pressure (CPAP) apparatus although the invention is not limited to such breathing apparatus—for example, the breathing apparatus could be a high flow therapy apparatus or any other pressure therapy apparatus such as PAP, Bi-level or the like). FIG. 2 shows a block diagram of such an apparatus. The breathing apparatus 10 shown could be any standard CPAP apparatus comprising an inlet for receiving ambient air, a blower for providing pressured air, a humidifier and an outlet for providing therapy to a patient (not shown). Details of breathing apparatus such as CPAP apparatus will be known to those skilled in the art and will only be described briefly here.

The breathing apparatus 10 comprises a housing, a humidifier 11 and a blower 12 controllable by a controller (such as a microprocessor, microcontroller or the like) 30. The controller operates the blower (based on operational parameters such as internal user definable and/or preset parameters) to take air from the inlet, pass it to the humidifier for humidification and out the outlet through the conduit to the patient.

Figure 3A:
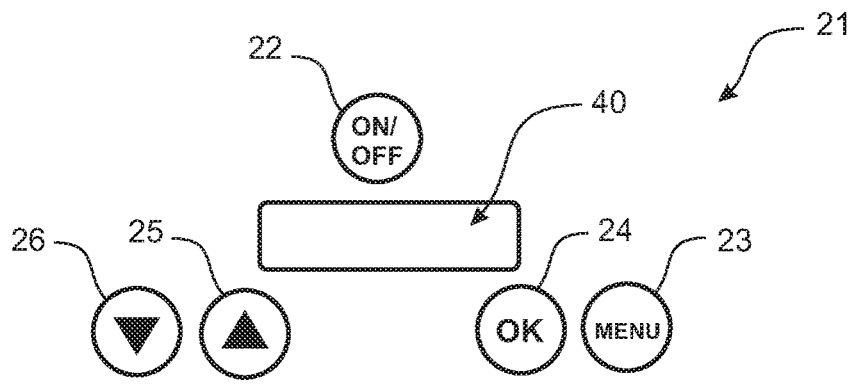
FIG. 3A is a schematic front view of the user interface according to an aspect of the present invention.

The apparatus has a user interface 20 coupled to the controller, as shown in FIG. 1 and schematically in FIG. 3A. User control of the breathing apparatus 10, including the setting of operational parameters, is done through use of the user interface 20. The user interface comprises a display 40, and buttons 23-26 for operating the display and setting the operational parameters of the breathing apparatus. The display 40 could comprise one or more of any suitable screen such as a (optionally colour) LCD or LED screen. The display is for displaying information such as: a home screen, time, icons, apparatus settings and other functionalities (more generally operational parameters) of the breathing apparatus 10. At least some of the information is arranged hierarchically in a menu system as or under selectable menu items 50. The menu items could be indicators for information, and/or embody actual information. The user interface 20 is configured as described in detail below for improved ease of use and to facilitate better user compliance.

In a preferred embodiment, the user interface 20 comprises five user inputs/controls (generally called buttons); a power button 22, a menu button 23, a confirmation (also termed selection) button 24, and two adjustment buttons 25, 26 for adjusting operational parameters of the breathing apparatus 10. The buttons can be any physical or touch buttons or any other suitable control operable by the user, such as tactile and non-tactile buttons, touch screens, levers and dials. All user interface buttons may have suitable logo or graphic overlays to help distinguish the buttons from each other, and to help a user recognise the buttons and their related functions. Input from the user input is passed to the controller. The buttons do not need to be labelled or named as described herein—any type of descriptor (text or otherwise) could be used. The buttons have been nominally defined as "menu", "confirm", "up" and "down" and "on/off" herein for identification and description purposes only. Any button, however labelled, that functions as described herein is considered to fall within the scope of the invention. For example, any up/down indicia could be shown, such as arrows or the like, on the up/down buttons.

Figure 3B:
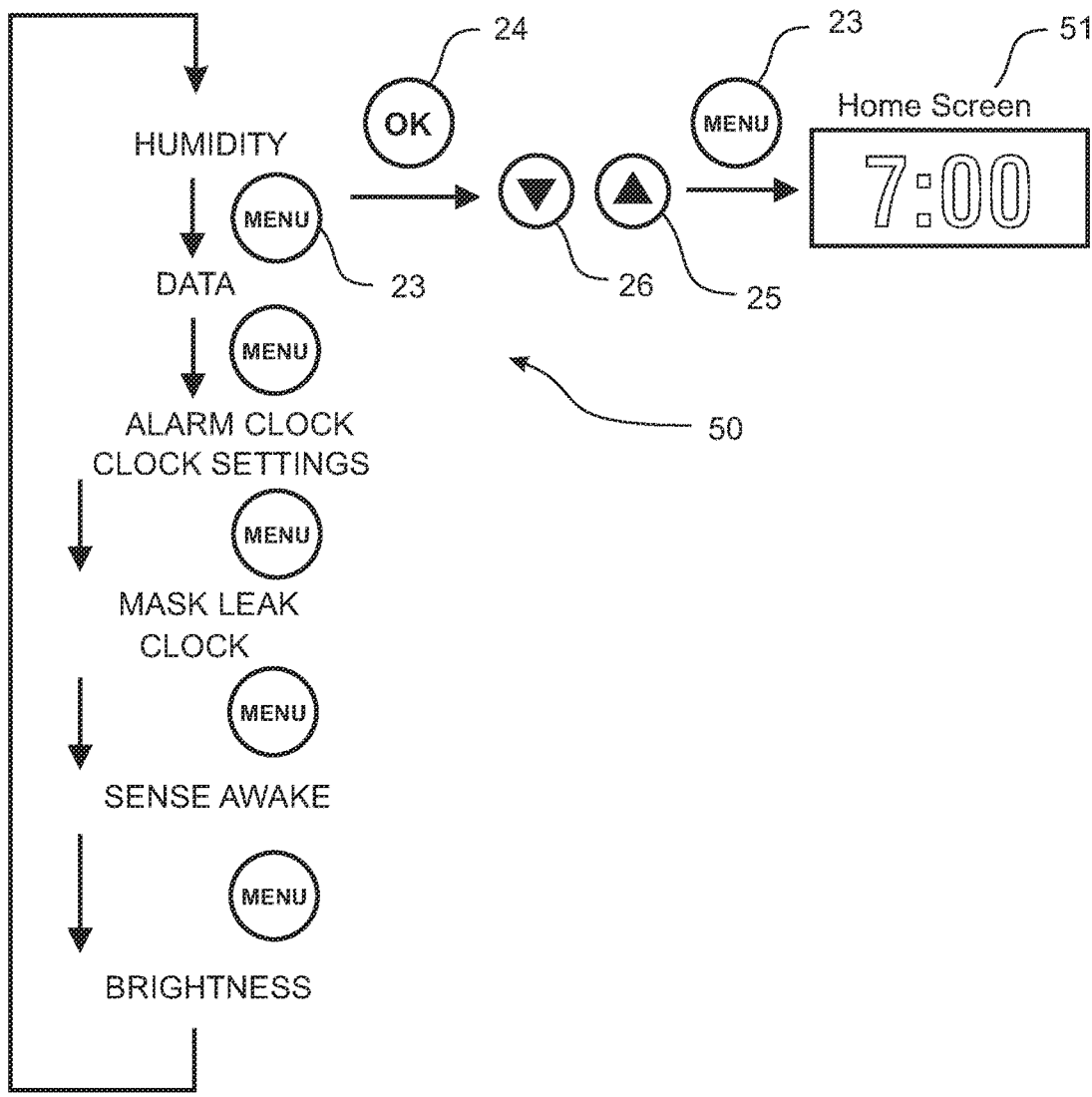
FIG. 3B is a schematic flow diagram of the user interface of FIG. 3A and possible menu items.

Operation of the user interface is described with reference to FIGS. 3A, 3B and 4. The power button 22 or on/off button, when initially pressed, sends a signal to the controller 30, which in turn activates the blower and/or exits standby mode to commence respiratory therapy. The power button 22 can also deactivate the blower and/or change to standby mode with a second press. In a preferred embodiment, the power button 22 functions instantly with a single press. In alternative embodiments, the power button may function after being pressed for a period of longer than a predetermined amount of time (e.g., longer than 1 second), or pressed several times in rapid succession. This added level of safety may prevent unintentional usage of the apparatus when the user did not intend to press the power button 22. In a preferred embodiment, the buttons may be designed to be flush with the front panel of the apparatus, which may also help in preventing unintentional pressing.

The display 40 defaults to the home screen 51, which may be configured to display information relating to current time as a digital clock. Alternatively, or in some configurations, the home screen 51 may be configured to display other information, such as information relating to the current humidity, or may be configured to display no information. Upon a user pressing the menu button 23, the controller 30 receives a signal indicating activation of the menu button, and operates the user interface 20 to scroll through a menu system comprising a number of hierarchical menu items, including a set of top level (may also be referred to as high-level) menu items 50. The menu items 50 enable control of respiratory settings/parameters, such as CPAP settings/parameters, and/or other breathing apparatus parameters. Therefore, the menu items can be termed "CPAP setting menu items" or more generally "respiratory setting menu items". CPAP settings are any CPAP related parameter values relating to operation of the CPAP apparatus and/or provision of CPAP therapy. More generally, respiratory settings are any respiratory parameter values or other breathing apparatus parameter values relating to operation of a breathing apparatus and/or provision of the therapy by the breathing apparatus.

Menu items 50 enable display and/or setting (control) of respiratory and/or other breathing apparatus parameters, such as (but is not limited to): information relating to user and device data; level of humidification; treatment pressure; ramp time; automatic ramp; wakefulness dependent pressure control (wherein wakefulness dependent pressure control refers to an algorithm developed by Fisher and Paykel Healthcare that detects the wakefulness of the patient and modulates the pressure of therapy in response "wakefulness dependent pressure control"); heated tube temperature; clock and time settings; an alarm with setting options for the alarm; screen brightness; leak such as mask leak and threshold for responding to mask leak; notification relating to presence of peripherals such as USB or network connection; home screen; and images relating to user feedback and vendor logos. Each top level menu item can optionally comprise one or more hierarchical levels of other (lower level) menu items and/or information. One or more of the hierarchical levels provides the opportunity for the user to set operation parameters relating to/associated with the menu item 50. The types of data displayed under user or device data may include information relating to therapy compliance, total hours used, and other usage data.

In the embodiment described, the set of top level menu items 50 comprises "humidity", "data", "alarm clock settings", "mask leak", "clock" (adjustment of clock), "wakefulness dependent pressure control", and "brightness", along with the home screen (e.g. time display) 51. When the menu button 23 is pressed, the controller 30 receives a signal from the button, and controls the display 40 to display the next top level menu item (in this case going from home screen 51 to "humidity"). Each time the menu button 23 is pressed by a user, the next top level menu item is displayed on the display 40 (e.g. "data"). Therefore, by pressing the menu button 23, the user can cycle ("scroll") through the set of top level menu items 50 in a continuous and/or sequential scrolling manner. With each successive press of the menu button 23, a successive top level menu item from the set is displayed on the display 50, replacing the previously displayed menu item. Once the last menu item is displayed, the next press of the menu button 23 results in display of the first top-level original menu item (e.g., home screen 51). The home screen can be in one option considered the first top-level menu item or alternatively be considered separate to the top level menu item. The menu button 23 is therefore used to cycle through the list of menu items 50 continuously and/or sequentially on the display 40. If at any stage in the top level menu the confirmation button is pressed, the controller will display the home screen 51.

Once the user has cycled to their desired menu item, if further configuration is available for the selected menu item 50 the controller 30 can control the user interface 20 to provide the opportunity for a user to set operational parameters. The two adjustment buttons 25, 26 or 'Up' and 'Down' buttons, may be used to configure/set operational parameters as per the menu items. The controller 30 receives input from the buttons 25, 26, and controls the user interface 40 to display the change of the associated operational parameter (s) (e.g. increase/decrease the parameter as per the pushing of the up and down buttons). Once the operational parameter (s) have been chosen, the user presses the confirmation (e.g. "OK" or tick) button 24 and the controller 30 changes the associated operational parameter(s) (such as settings or functionality) in its memory accordingly, and displays the parameter on the display 40. The controller then displays the home screen again 51. Alternatively, if the user has changed the operational parameter(s) in error or does not wish to change the operational parameter(s) in memory, instead of pressing the confirmation button 24 the user may press the menu button 23 to trigger the controller 30 to cycle 28 directly to the home screen 51.

If further configuration is not available for the selected menu item 50, but there exists a subsequent level of menu items in the hierarchy (for example, if the selected menu item 50 is 'data' and the subsequent level of menu items under 'data' comprises a plurality of data screens), then the two adjustment buttons 25, 26, or 'Up' and 'Down' buttons, may be used to cycle through subsequent levels of menu items in the hierarchy and/or information. Either the menu button 23 or confirmation button 24 then may be pressed to cycle through to the home screen 51/first top level menu item. If a top level menu item has sub menus, but the 'Up' and 'Down' buttons are not pressed, pressing the menu button will cycle to the next top level menu item, and pressing the confirmation button will display the home screen/first top level menu item.

Figure 4:
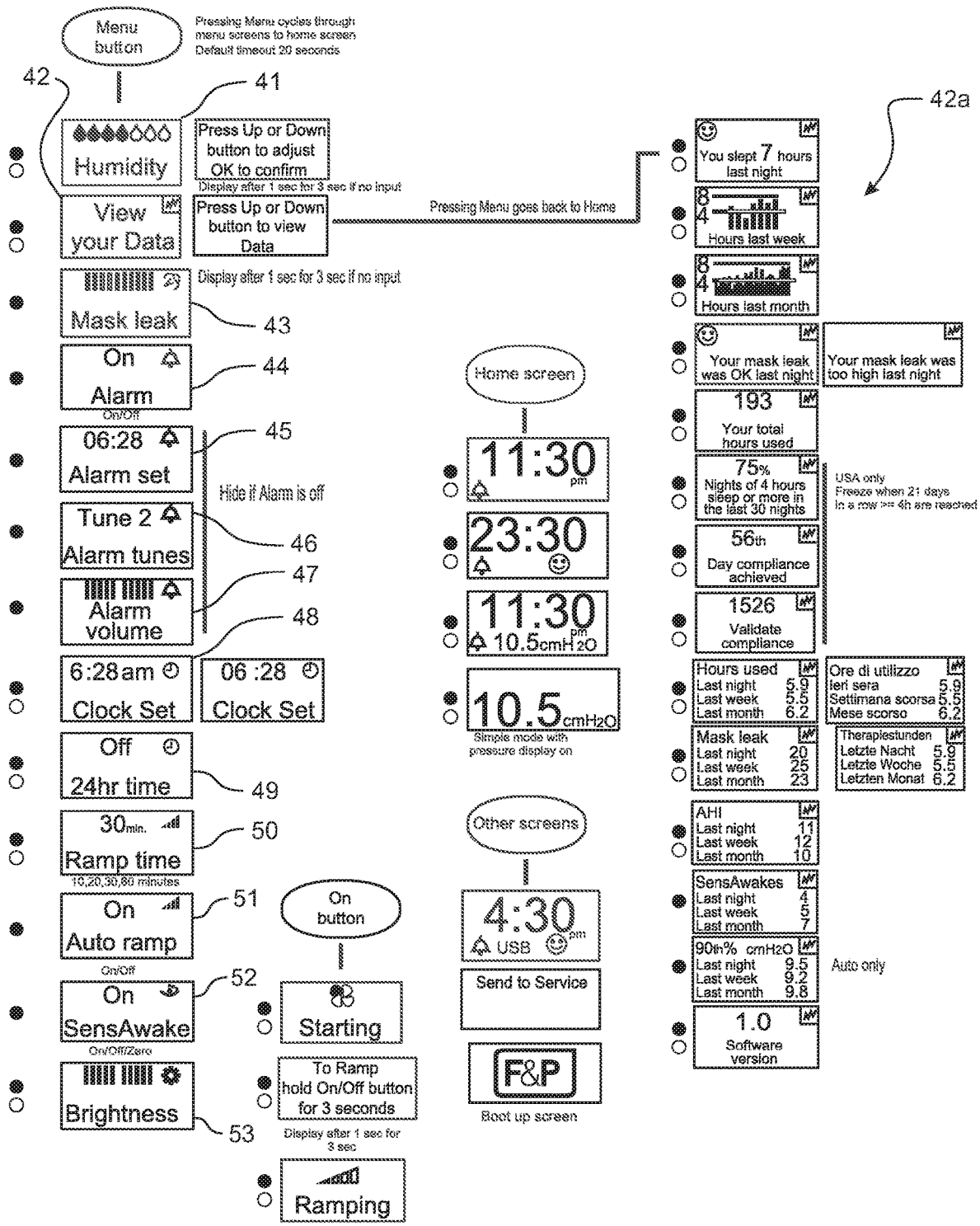
FIG. 4 is a more detailed schematic flow diagram of the user interface and possible menu items.

FIG. 4 shows various screen shots of the display with various menu items and information as an example of some of the settings that can be made in this manner. The humidity menu item 41 can be cycled to and selected using the menu button 23, and then the humidity parameter can be set (adjusted up or down) by pressing the up/down buttons 25, 26 The controller 30 receives input and operates the user interface 20 to show the humidity by highlighting the appropriate number of water drops in the humidity menu item icon 41. The confirm/confirmation ("ok" or tick) button 24 can be pressed to confirm the parameter change, and then display the home screen, or the menu button can be pressed to cancel the change and return to display the home screen. Alternatively, if the up and down buttons are not used to change the humidity the view data menu item 42 can be cycled to and displayed using the menu button. At that point, if the confirm button is pressed, the controller will return to and display the home screen, or if the menu button is pressed, the controller cycles to and displays the next top level menu item. Alternatively, using the up/down buttons 25, 26 any of the data information in the lower level 42a menu (as shown in the screen shots in FIG. 4) can be displayed. When in the lower level menu 42a, the controller 30 receives the input from the up down buttons 25, 26 and control the user interface 40 to cycle through and display the appropriate information on the display 40. After using the up/down arrows to cycle through the lower level menu items 42a, the confirm or menu button can be pressed, which will cause the controller to return to and display the home screen.

The mask leak 43, alarm volume 47 and brightness 53 menu items can be sequentially displayed by cycling through using the menu button and then can have their parameters set using the up/down buttons 25, 26 in the same manner as described for the humidity menu item 41, and the icons displayed as appropriate. The menu and confirmation buttons work in the same way. Similarly, upon the alarm can be turned on and off 44; the alarm time set 45; the alarm tune selected 46; the clock set 48; the 24 hour time selected 49; the ramp time adjusted 50; auto ramp turned on and off 51; wakefulness dependent pressure control turned on and off 52 using the up/down buttons 25, 26 as appropriate. Other menus are also shown comprising on button menu, home screen, and other screen menu. These can be selected and cycled through using the menu button 23 and ok button 24 as previously described.

In summary, a user may program or control the breathing apparatus 10 via the user interface 20. The user may turn the blower of the breathing apparatus 10 on or off by triggering or activating the power button 22. The apparatus 10 may display the home screen on the display 40. The user may then press the menu button 23 to cycle through and display subsequent menu items 50 on the list (for example see FIG. 3B flow chart). Pressing the confirm button will cause the controller to skip to and display the home screen. If a menu item contains adjustable parameters or lower level menu items, pressing the adjustment buttons 25, 26 allows the user to adjust the parameters or select between/cycle through lower level menu items accordingly. If parameters are adjusted, the confirm button will accept the adjusted parameter and then cause the controller to display the home screen. Alternatively, once the up/down buttons are pressed, pressing the menu button will reject the change and cause the controller to display the home screen. If lower level menu items are cycled through using the adjustment buttons 25, 26, then pressing either the confirmation button 23 or menu button will cause the controller to display the home screen. While the display 40 is displaying any screen other than the home screen or the basic (top level) menu items, pressing the menu button 23 or confirm button will cause the controller to the display 40 to display the home screen.

Preferably, the display 40 will display only one menu item 50 at a time. In an alternative embodiment, more than one menu item 50 may be displayed on the display 40 at any given time. In this case, when the menu button 23 is used to cycle through menu items, the oldest menu item will be removed from the display and the more recent menu item(s) will be displayed along with the next menu item in the seat. Possibly, the display screen 40 could be split so that the time is displayed on one side and the menu items/information displayed on the other. The home screen would then default to a blank screen or some other menu option.

In an alternative, the menu button 23 could be pressed instead of the 'OK' button 24 when confirming a selected parameter value. Thus the selected parameter value and the change of the menu item could occur simultaneously. Yet other actions could occur when pressing the confirmation and/or menu buttons at different points in the menu cycle/hierarchy.

The embodiment above describes the options of a top level menu item that is adjustable, or a top level menu item that has lower menu items that can be cycled through and viewed. In another possibility, a top level menu item might have lower level menu items that themselves are adjustable. These lower level menu items could be cycled using, and the adjustment of their parameters could be made, using the up/down buttons as described above. The menu and confirmation buttons could work in the same way as described above.

The user interface could be an OEM component that is manufactured separately by another party, or it could be manufactured and incorporated into the breathing apparatus by the same party.

Second Embodiment

Figure 5:
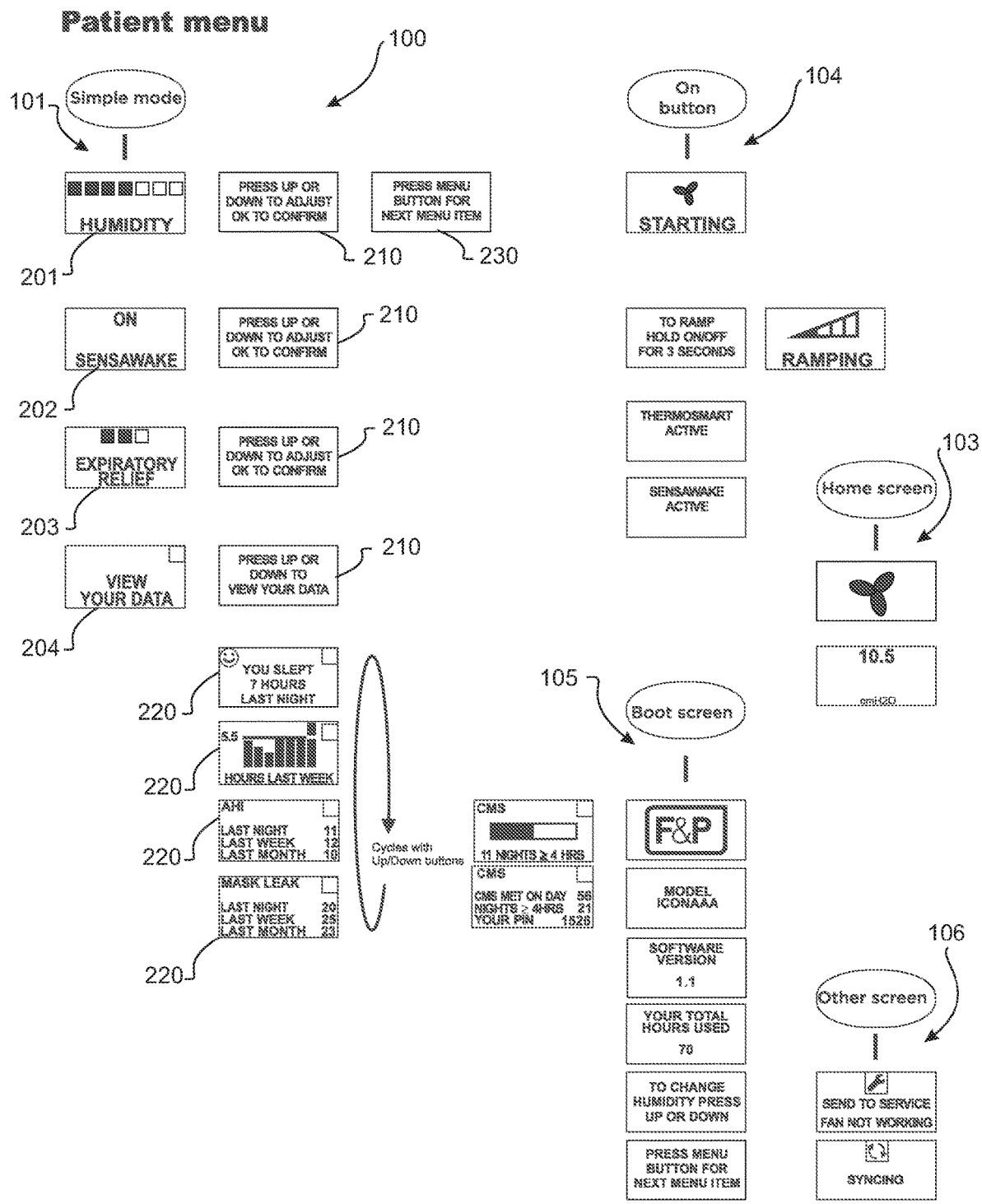
FIG. 5 is a detailed schematic flow diagram of a patient menu of the second embodiment.

Another embodiment of the user interface 20 is described with reference to FIGS. 5 and 6. The user interface 20 is substantially the same as described above, which comprises a display 40, and buttons 22-26 for operating the display, displaying information to the user and setting the operational parameters of the breathing apparatus. The display 40 could comprise one or more of any suitable screen such as (optionally colour) LCD or LED screen. The user interface 20 is configured as described in detail below for improved ease of use and to facilitate better user compliance.

The display 40 is configured to display selectable menu items 100. The menu items 100 enable control of respiratory settings/parameters, such as CPAP settings/parameters, and/or other breathing apparatus parameters. Therefore, the menu items can be termed "CPAP setting menu items" or more generally "respiratory setting menu items". CPAP settings are any CPAP related parameter values relating to operation of the CPAP apparatus and/or provision of CPAP therapy. More generally, respiratory settings are any respiratory parameter values or other breathing apparatus parameter values relating to operation of a breathing apparatus and/or provision of the therapy by the breathing apparatus.

The menu items 100 could be indicators/indicia for information, and/or embody actual information. The menu items may be categorised or grouped into different menu groups, such as a patient menu 101, clinician menu 102, home screen menu 103, therapy operating menu 104, boot screen menu 105 and other miscellaneous menus 106. Each set of menus comprises a number of hierarchical menu items, including a set of top level menu items and sets of lower level menu items. The lower level menu items are usually associated with configuring settings related to the corresponding top level menu item.

A possible list of top level menu items for the patient menu 101 comprises but is not limited to: humidity control 201 therapy pressure settings control; wakefulness dependent pressure control turned on and off control 202 (SensAwake™); expiratory relief 203; viewing data 204; leak settings and temperature control. Viewing data 204 is associated with one or more corresponding lower level menus related to displaying performance metrics or compliance data, for example lower level menus comprises accumulative time patient was asleep, number of hours slept over time, AHI data, mask leak data, CMS data and other personal statistics.

Operation of the user interface according to the second embodiment will now be described with reference to FIGS. 5 and 6. The apparatus is powered on goes into standby mode when it is connected to power (such as a power socket in the wall). A boot screen 105 will be displayed on the user interface 20 upon first powering on/plugging in the apparatus 10. The boot screen 105 may cycle through a series of information screens, this for example could include a manufacturer graphic/logo or splash screen, device model number, software version number, total hours used and/or other information. The boot screen 105 may end with messages prompting the user to press the up/down buttons 25, 26 to change humidity, and to press menu button 23 for the next menu.

After the apparatus has completed the boot screen 105 sequence, the user may start the therapy by pressing the on/off button 22. A therapy operating menu 104 will be displayed. The operating menu 104 may show a static or animated graphic of a fan and/or other indicia corresponding to the status of the therapy. The therapy operating menu 104 automatically cycles through number of information screens, including a ramp prompt screen (where a CPAP ramp can be initiated), and statuses of installed features such as Thermosmart™ a heated breathing tube and wakefulness dependent pressure control (SensAwake™). At the ramp prompt screen, the user may optionally hold the on/off button 22 for a predetermined period of time, for example 3 seconds, to turn on ramp therapy. The actual ramping is pre-set by the manufacturer or clinician. The user may also press the on/off button 22 while the therapy is active to stop the therapy.

At any time while the apparatus is turned on, the user may press the menu button 23 to cycle through the set of top level patient menu 101 items and the home screen 103. The home screen 103 could be blank, a clock, a static or animated symbol/graphic of a fan showing the current status of the therapy. In one embodiment, the current pressure level display may be activated after 20 second of inaction.

Pressing the menu button 23 continuously and/or sequentially cycles/scrolls through the top level patient menu 101 items, for example humidity control 201, wakefulness dependent pressure control turned on and off settings 202, expiratory relief settings, 203 and viewing data 204. Each press of the menu button cycles to the next menu item. With each successive press of the menu button 23, a successive top level menu item from the set is displayed on the display 50, replacing the previously displayed menu item. Once the last menu item is displayed, the next press of the menu button 23 results in display of the first top-level original menu item (e.g., home screen 51). The menu button 23 is therefore used to cycle through the list of menu items 50 continuously and/or sequentially on the display 40.

While at any one of the top level menu items, pressing up/down buttons 25, 26 will correspondingly change (configure or set) the operational parameter associated with that menu item—for example, level of humidity, turn on/off the wakefulness dependent pressure control feature, adjust level of expiratory relief or view detailed data. Pressing the OK button 24 or similar confirmation button confirms the adjustment—and optionally the display defaults back to the menu item, or in an alternative embodiment the home screen. In an alternative embodiment, after a set time (such as three seconds) the change is adopted automatically. If a top level menu item is cycled to, and no action is detected the top level menu over a defined time, such as 3 seconds, then another screen 210 is displayed to prompt the user to use the up/down buttons 25, 26 to adjust the corresponding settings. If a further defined time elapses (e.g. 3 seconds) before action is detected, then a further screen 230 is displayed prompting the use to press the menu button to cycle to the next top level menu item. Pressing up/down buttons 25, 26 at the viewing data 204 menu item will cycle through a number of lower level display items 220 such as performance metrics and compliance data, hours slept last night or over time, and other metrics such as AHI, mask leak and CMS. The same action could occur for any other menu item that has lower level display items.

When cycled to a top level (or lower level) menu item, in one embodiment, pressing up or down buttons 25, 26, adjusts the value of the settings in a corresponding manner. For example up or down buttons 25, 26 may increase or decrease the humidity level; turn wakefulness dependent pressure control on/off, and/or adjust expiratory relief. In an alternative embodiment, pressing up or down buttons 25, 26 cycles through fixed settings, for example both up and down buttons 25, 26 may serve the purpose of cycling the humidity level and/or expiratory relief setting from 1 to 2 to 3 then off and back to 1 again. Pressing the menu button will return the display to the home screen again.

In one embodiment, pressing the up/down buttons 25, 26 (or optionally any other button) at the home screen 103 will take the user to a default menu item. The default menu item may be the humidity settings 201 menu, for example. The initial press of the up/down button 25, 26 will not have the effect of cycling the menu or adjusting setting levels, it will simply take the user to the default menu item. This provides a quick way to reach a commonly used or desired menu item. Additional pressing of the up/down buttons 25, 26 would then adjust the default menu item or the humidity settings accordingly. In alternative embodiments, the apparatus may be configured to take the user to a first menu item, a pre-configured menu item, the most frequently used menu item, or the last chosen menu item, by pressing the up/down buttons 25, 26 at the home screen 103. In one embodiment, the user or clinician may choose the default menu item.

Figure 6:
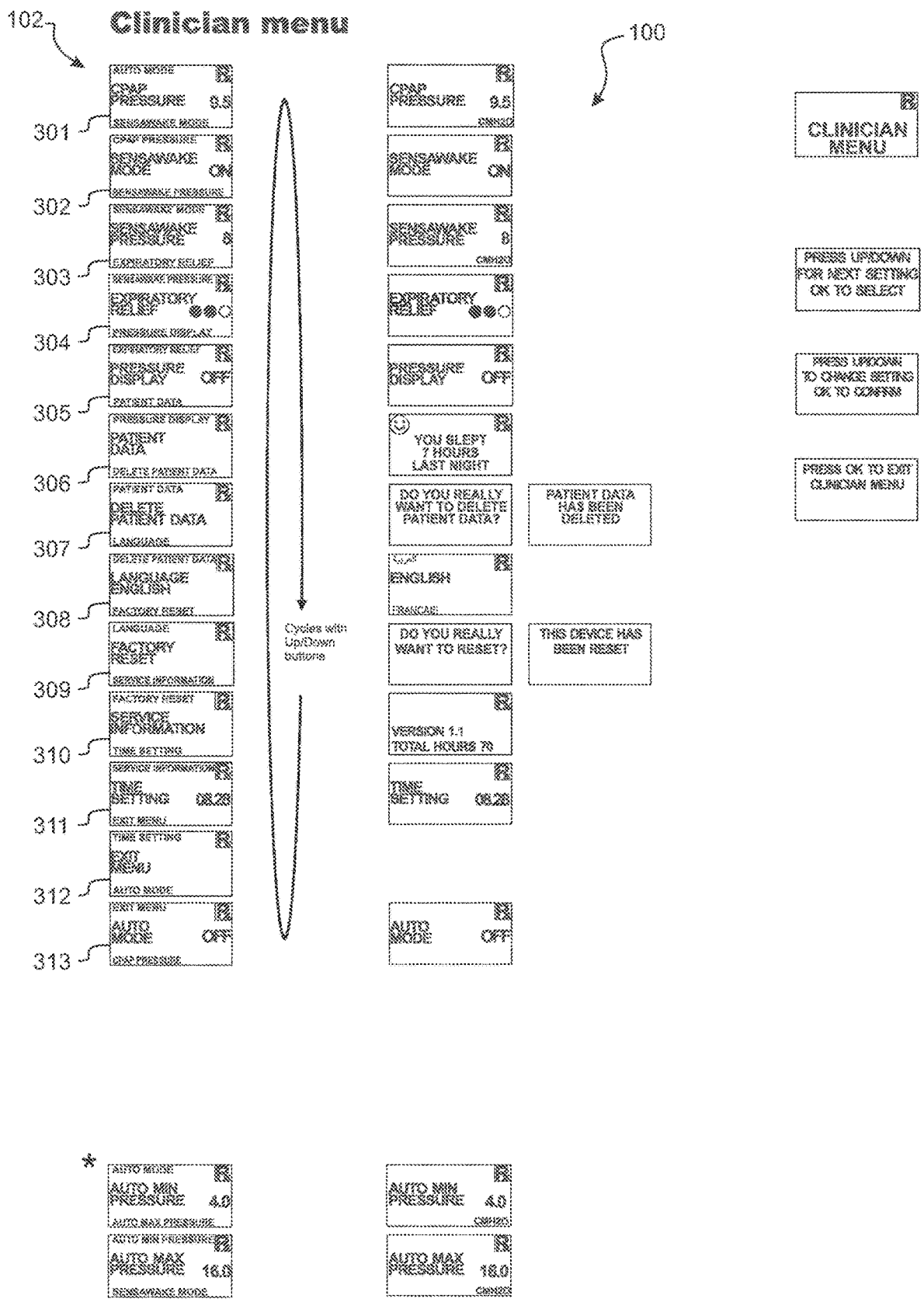
FIG. 6 is a detailed schematic flow diagram of a clinician menu of the second embodiment.

Referring to FIG. 6. A possible list of top level menu items for the clinician menu 102 comprises but is not limited to: CPAP pressure settings 301; therapy pressure settings control; wakefulness dependent pressure control mode (SensAwake™) mode 302; SensAwake™ pressure 303; expiratory relief 304; pressure display 305; patient data 306; delete patient data 307; language settings 308; factory reset 309; service information 310; time settings 311; exit menu 312; auto mode 313; leak settings; and temperature control. Each of the top level menu items may have a corresponding lower level menu item for changing settings, viewing data or confirming setting changes. The miscellaneous or servicing menus 106 may comprise information screens such as send to service, diagnostic, and data synchronisation messages.

Upon a combination of key presses the user or clinician may access a hidden clinician menu 102. One combination for accessing the clinician menu 102 is to press the on/off button 22 in conjunction with any other button for 3 seconds. The clinician menu may display a splash or welcome screen for a predetermined time period. Pressing the OK button 24 will bypass the splash screen. Pressing the on/off button 22 will exit the clinician menu immediately and take the user to the home screen 103. The user may also exit the clinician menu 102 by pressing the menu button 23 and pressing the OK button 24 upon confirmation of exit.

While under the clinician menu 102, the user may press up/down buttons 25, 26 to cycle through top levels menu items as described above. The user may press the OK button 24 to select the top level menu items to display a corresponding lower menu item for further configuration. If no action is detected after a predetermined period of time, for example 3 seconds, then a message is displayed to remind the user to do so. At the lower menu item, the user may press up/down buttons 25, 26 to change or cycle through settings and press the OK button 24 to confirm the change. Again, if no action is detected after a predetermined period of time, for example 3 seconds, then a message is displayed to remind the user to do so.

For menu items which are either on or off functions and requires confirmation from the user, the user may press the OK button 24 to confirm the selection. For example, to activate the SensAwake™ feature (wakefulness dependent pressure control), the user may navigate to the SensAwake™ setting menu item 202, then press up/down buttons 25, 26 to display a corresponding lower level menu item indicating whether to turn the feature on or off. The user can then confirm the selection by pressing the OK button 24 at the corresponding lower level menu. If no action or press of the OK button 24 is detected at the lower menu item for a predetermined period of time, for example 3 seconds, then the user interface will return to the high level menu item without making any changes to the settings. In an alternative embodiment, if no action is detected at the lower menu item after a predetermined period of time, the apparatus will accept the chosen setting (either on or off) corresponding to the lower level menu item that is displayed without requiring confirmation from the OK button 24. For example the system will accept the settings as displayed after 3 seconds without requiring user confirmation from using the OK button 24.

While pressing the up/down buttons 25, 26 cycles through settings or top level menus (in the case of the clinician menu 102), holding down the up/down buttons 25, 26 will also serve the same function. Further, pressing or holding down the up/down buttons 25, 26 will continuously cycle through the settings or menu items. In other words, after reaching the end of the menu items list the user interface will return to displaying the first item. The up/down buttons 25, 26 is therefore used to cycle through the list of menu items continuously and/or sequentially. In an alternative embodiment, the settings or menu items do not automatically jump back to the first setting or menu item, and will stop cycling once the setting or menu item reaches the end of the setting options or the menu items list. In a further embodiment, holding down the up/down buttons 25, 26 continuously may speed up the rate at which the settings or menus are cycled or displayed.

The default time-out interval for inaction is 20 seconds, after which the user interface 20 will reset the menu displayed to the home screen 103. The time-out intervals may be configurable.

The user interface 20 may have buttons 22-26 comprising any suitable indicia displayed thereon to indicate their function (e.g. arrows, ticks, symbols, words, letters, numbers or the like). For example the up/down buttons 25, 26 can be words, or the symbolic arrows showing up or down or a combination of both. The buttons 22-26 may be physical or touch buttons, capacitive display buttons, touch screens, tactile or non-tactile buttons, depressable buttons, membrane buttons or any other suitable buttons or other control known in the art.

The menu items described above are just examples for exemplary purposes and are neither limiting nor exhaustive. The menu structure and operation could work with any menu items.

The display screen could show navigation indicia indicating how many menus there are and/or which menu the user is currently in. One such non-limiting example is a scroll bar.

The embodiments described are by way of example only and are not limiting.

What is claimed is:

1. A breathing apparatus with a user interface comprising:
    a blower;
    a display that presents a home screen and at least one menu item; and
    three buttons that operate the display and the breathing apparatus using the display,
    the three buttons comprising:
        a first button that, in a first mode, sequentially cycles through and displays the home screen and the at least one menu item;
        a second button and a third button that, in the first mode, changes a parameter of the at least one menu item when the at least one menu item is presented on the display, the parameter comprising at least one of a respiratory parameter and a breathing apparatus parameter;
        the first button, in the first mode, confirming change of the parameter of the at least one menu item following the change to the parameter;
        the second button, in a second mode, cycling upwardly through a plurality of top level menu items and a third button, in the second mode, cycling downwardly through the plurality of top level menu items; and
        the first button, in the second mode, selecting at least one of the plurality of top level menu items to display a corresponding lower menu item for further configuration.

2. The breathing apparatus of claim 1 further comprising a humidifier with an outlet that delivers therapy to a patient.

3. The breathing apparatus of claim 2 further comprising a power button, the power button turning the breathing apparatus on or off, the power button functioning after being pressed for a period longer than a predetermined amount of time.

4. The breathing apparatus of claim 3, wherein a boot screen is displayed on the display upon powering on the breathing apparatus, the boot screen cycling through a sequence of information screens, the sequence of information screens comprises at least one of:
    a manufacturer graphic or splash screen;
    a device model number;
    a software version number; and
    a total hours operated;
    wherein, after the breathing apparatus has completed the sequence of information screens, a therapy operating menu is displayed, the therapy operating menu comprises:
    a static or animated graphic of a fan or an indicia corresponding to a status of the therapy.

5. The breathing apparatus of claim 1, wherein, when in the first mode, the second button increases a value of the parameter of the at least one menu item, the third button decreases the value of the parameter of the at least one menu item, and the first button confirms the value of the parameter of the at least one menu item and, responsive to the first button confirming the value of the parameter of the at least one menu item, the display presents a next menu item in a list of menu items or the home screen.

6. The breathing apparatus of claim 1, wherein, when in the first mode, the second button and the third button sequentially cycle through a plurality of lower level menu items on the display.

7. The breathing apparatus of claim 6, wherein, when in the first mode, after sequentially cycling through the plurality of lower level menu items, the home screen is presented again on the display.

8. The breathing apparatus of claim 1, wherein the breathing apparatus comprises a high flow therapy apparatus, and the at least one of the respiratory parameter and the breathing apparatus parameter comprises a respiratory parameter value or a breathing apparatus parameter value associated with operation of the breathing apparatus or provision of high flow therapy with the breathing apparatus.

9. The breathing apparatus of claim 1, wherein the home screen displays information associated with a current respiratory parameter or a current breathing apparatus parameter.

10. The breathing apparatus of claim 9, wherein a portion of the home screen is blank.

11. The breathing apparatus of claim 10, wherein the home screen comprises at least one of a clock and a static or animated graphic of a fan showing a current status of a therapy.

12. The breathing apparatus of claim 1, wherein, when in the first mode, the at least one menu item comprises a humidity control menu item that adjusts a humidity parameter, and viewing data related to displaying one or more of:
performance metrics,
compliance data, and
information relating to therapy compliance, total hours used, and other usage data.

13. The breathing apparatus of claim 12, wherein, when in the first mode, responsive to displaying the viewing data, at least one of the second button and the third button cycles through a plurality of lower level display items, the plurality of lower level display items comprising one or more of the performance metrics, the compliance data, hours slept for a previous night, hours slept over time, data associated with hours using the breathing apparatus for the previous night, and data associated with the hours of using the breathing apparatus over a previous week.

14. The breathing apparatus of claim 1, wherein, when in the second mode, a clinician menu is accessible responsive to at least two of the three buttons being pressed for a set period of time, and wherein, while displaying the clinician menu, the second button or the third button may be pressed to change settings.

15. The breathing apparatus of claim 1, wherein, in the second mode, when the lower menu item for configuration is selected, the second button changes or cycles through settings for the lower menu item, the third button also changes or cycles through settings for the lower menu item, and the first button confirms the settings for the lower menu item and, responsive to the first button confirming the settings of the lower menu item, the display reverts to the plurality of top level menu items.

16. A method of operating a breathing apparatus comprising a blower, a display configured for displaying one or more menu items, and three buttons configured for operating the display and the breathing apparatus via the display, the method comprising:
displaying a home screen;
in a first mode, receiving a first input from a first button being pressed;
responsive to receiving the first input, sequentially displaying a first menu item of a set of menu items and each subsequent menu item in the set of menu items;
receiving a second input from either a second button or a third button being pressed;
responsive to receiving the second input, either:
displaying a change in a parameter associated with a displayed menu item, or
displaying a plurality of data or menu item from a lower level menu;
the parameter comprising a respiratory parameter or a breathing apparatus parameter;
displaying the home screen after sequentially cycling through and displaying each menu item of the set of menu items;
in a second mode, receiving a third input from a combination of buttons being pressed;
following receipt of the third input, sequentially displaying a series of top level menu items in response to a fourth input from either the second button or the third button being pressed;
receiving a fifth input from the first button and, responsive to the fifth input, displaying a menu item from a lower level menu for further configuration; and
displaying the home screen after sequentially cycling through and displaying each menu item of the top level menu items.

17. The method of claim 16, wherein the breathing apparatus further comprising a humidifier comprising an outlet for providing therapy to a patient.

18. The method of claim 16 further comprising:
receiving an input from the first button;
confirming the change in the parameter; and
displaying a subsequent menu item in the set of menu items or the home screen.

* * * * *